United States Patent [19]

Satoh

[11] Patent Number: 5,474,906
[45] Date of Patent: Dec. 12, 1995

[54] REAGENT FOR DETERMINING γ-GLUTAMYL TRANSPEPTIDASE ACTIVITY

[75] Inventor: Kazuhiko Satoh, Tochigi, Japan

[73] Assignee: Eiken Kagaku Kabushiki Kaisha, Tokyo, Japan

[21] Appl. No.: 216,060

[22] Filed: Mar. 22, 1994

[30] Foreign Application Priority Data

Mar. 26, 1993 [JP] Japan ................... 5-092169

[51] Int. Cl.⁶ ................... C12Q 1/48; C12Q 1/00; C12Q 1/37; C12Q 1/52
[52] U.S. Cl. ................... 435/15; 435/4; 435/24; 435/16
[58] Field of Search ................... 435/15, 4, 24, 435/28, 805, 810, 16; 514/18; 424/8

[56] References Cited

U.S. PATENT DOCUMENTS

| | | | |
|---|---|---|---|
| 3,878,048 | 4/1975 | Carroll | 435/15 |
| 3,892,631 | 7/1975 | Carroll | 435/15 |
| 3,979,447 | 9/1976 | Bernt et al. | 435/15 |
| 3,986,931 | 10/1976 | Bernt et al. | 435/15 |
| 4,049,702 | 9/1977 | Bernt et al. | 435/15 |
| 4,177,109 | 12/1979 | Tohyama et al. | 435/24 |
| 4,281,181 | 7/1981 | Nagasawa et al. | 424/8 |
| 4,336,331 | 6/1982 | Nagasawa et al. | 424/8 |
| 4,425,427 | 1/1984 | Luderer | 435/15 |
| 4,560,650 | 12/1985 | Bauer, III et al. | 435/15 |
| 4,567,138 | 1/1986 | Beck et al. | 435/15 |
| 4,603,107 | 7/1986 | Deneke et al. | 435/15 |
| 4,675,290 | 6/1987 | Matsumoto et al. | 435/24 |
| 4,801,580 | 1/1989 | Kitaura et al. | 514/18 |
| 4,851,572 | 7/1989 | Ogata et al. | 435/15 |
| 4,879,221 | 11/1989 | Tokuda et al. | 435/15 |

FOREIGN PATENT DOCUMENTS

| | | |
|---|---|---|
| 0258473 | 3/1988 | European Pat. Off. . |
| 0297607 | 1/1989 | European Pat. Off. . |

OTHER PUBLICATIONS

Clinica Chimica Acta, vol. 65, pp. 21–27 (1975).
Clinica Chimica Acta, 315F–338F (1983).

*Primary Examiner*—Michael G. Wityshyn
*Assistant Examiner*—Louise N. Leary
*Attorney, Agent, or Firm*—Nixon & Vanderhye

[57] ABSTRACT

A reagent for determination of γ-GTP activity containing L-γ-glutamyl-3-carboxy-4-nitroanilide or a salt as a substrate and a transition metal ion or salt, a method for stabilizing L-γ-glutamyl-3-carboxy-4-nitroanilide using a transition metal ion salt, and a method for determining γ-GTP activity using this reagent. The transition metal ion or salt effectively prevents non-enzymatic decomposition (hydrolysis) of the substrate, thereby making it possible to supply the reagent as a solution.

26 Claims, No Drawings

REAGENT FOR DETERMINING γ-GLUTAMYL TRANSPEPTIDASE ACTIVITY

FIELD OF THE INVENTION

This invention relates to the determination of γ-glutamyl transpeptidase (EC 2.3.2.1, hereinafter abbreviated as γ-GTP) activity. γ-GTP is an enzyme catalyzing hydrolysis of γ-glutamyl peptide and transferring the hydrolysis product, γ-glutamyl group, to other peptides or L-amino acids. While γ-GTP widely occurs in the body, it is known that the γ-GTP activity in the liver and the serum increases with the development of various hepatic diseases. Therefore, γ-GTP activity determination is an essential clinical examination marker (or indicator) for diagnosing hepatic diseases.

BACKGROUND OF THE INVENTION

Various synthetic substrates for γ-GTP activity determination have been proposed. Widely employed substrates among them are L-γ-glutamyl-p-nitroanilide or a salt thereof and L-γ-glutamyl-3-carboxy-4-nitroanilide or a salt thereof which generate p-nitroaniline or 3-carboxy-4-nitroaniline (i.e., 5-amino-2-nitrobenzoic acid), respectively, by the enzymatic action of γ-GTP. For determining γ-GTP, the thus generated product is determined by spectrophotometry.

However, L-γ-glutamyl-p-nitroanilide or its salt, when dissolved in a buffer solution for γ-GTP activity determination, is precipitated as crystals over time due to poor solubility. Additionally, it undergoes non-enzymatic decomposition (hydrolysis) and releases p-nitroaniline when stored over a period of time. On the other hand, L-γ-glutamyl-3-carboxyl-4-nitroanilide or its salt, while having a high solubility, is also non-enzymatically decomposed (hydrolyzed) to release 3-carboxy-4-nitroaniline during storage.

Various studies have been conducted in order to overcome these problems. With respect to L-γ-glutamyl-p-nitroanilide, for example, it has been proposed to improve solubility by the addition of an acid, an organic solvent, a surfactant, etc. (see *Clinica Chimica Acta*, Vol. 65, p. 21–27 (1975)). Addition of cyclodextrin (see JP-A-57-74099 corresponding to WO-8201564 (U.S., DE), the term "JP-A" as used herein means an "unexamined published Japanese patent application") or a crown ether (see JP-A-60-16599) is suggested for improvement of solubility and inhibition of non-enzymatic decomposition (hydrolysis). Nevertheless, a technique for satisfying both solubility and stability of this substrate has not yet been developed.

Also with reference to L-γ-glutamyl-3-carboxy-4-nitroanilide, no effective means to inhibit non-enzymatic decomposition (hydrolysis) has been reported. Accordingly, because of the difficulty in supplying L-γ-glutamyl-3-carboxyl-4-nitroanilide in solution, the substrate must be supplied as a freeze-dried product or as a powder package to be dissolved in a buffer solution at the time of use. Moreover, since the pot life of the thus prepared substrate solution is only about 1 month even in a refrigerator (2° to 8° C.) due to non-enzymatic decomposition (hydrolysis), the clinical technician must prepare fresh substrate solution as needed and often each time an assay is conducted.

Inhibition of L-γ-glutamyl-3-carboxy-4-nitroanilide from non-enzymatic decomposition (hydrolysis) would make it possible to provide a solution-type reagent free from precipitation thereby eliminating the need for preparing fresh solution each time an assay is conducted.

SUMMARY OF THE INVENTION

An object of the present invention is to provide a reagent for γ-GTP determination comprising an aqueous solution of L-γ-glutamyl-3-carboxy-4-nitroanilide or a salt thereof (hereinafter sometimes referred to as "the substrate") in which the substrate has increased stability and is prevented from non-enzymatic hydrolysis.

Another object of the present invention is to provide a method for stabilizing L-γ-glutamyl-3-carboxy-4-nitroanilide or a salt thereof.

A further object of the present invention is to provide an economical method for determining γ-GTP activity.

The present inventor has found that the above objects are accomplished by the addition of a transition metal ion or salt to the reagent.

The present invention relates to a reagent for γ-GTP determination comprising L-γ-glutamyl-3-carboxy-4-nitroanilide or a salt thereof as a substrate and stabilizing amount of a transition metal ion or salt, a method for stabilizing L-γ-glutamyl-3-carboxy-4-nitroanilide, and a method for determining γ-GTP activity.

DETAILED DESCRIPTION OF THE INVENTION

The reagent is usually composed of at least a buffer solution containing the substrate (hereinafter referred to as liquid A) and a buffer solution containing an amino acid or peptide to which a γ-glutamyl group produced from the substrate by the enzymatic action of γ-GTP is transferred (hereinafter referred to as liquid B).

γ-GTP determination using the above-mentioned two-part liquid reagent can be carried out by mixing a sample to be assayed with liquid A and adding liquid B to the mixture, or mixing a sample with liquid B and then adding liquid A thereto. In either case, non-enzymatic hydrolysis of the substrate can be sufficiently prevented in the presence of a transition metal ion or salt.

Salts of L-γ-glutamyl-3-carboxy-4-nitroanilide which can be used in the present invention are not particularly limited, and the kind of the salt does not make any substantial difference to the essence of the present invention. An ammonium salt is generally used. The substrate is used generally in an amount of from 1 to 50 mM.

Examples of the amino acid or peptide to which a γ-glutamyl group is transferred include glycylglycine and glycylglycylglycine, and glycylglycine is particularly preferable. The amino acid or peptide is used generally in an amount of from 10 to 1,000 mM.

The transition metal which can be used in the present invention includes copper, nickel, and cobalt. Copper is particularly preferable as the transition metal, and both Cu (II) and Cu (I) have a sufficient stabilizing activity. The transition metal is added to the substrate solution in the form of an appropriate salt, and the type of salt is not particularly limited. Specific but non-limiting examples of suitable transition metal salts include copper (II) salts, e.g., copper (II) acetate, copper (II) citrate, copper (II) formate, copper (II) gluconate, copper (II) oleate, copper (II) oxalate, copper (II) phthalate, copper (II) bromide, copper (II) chloride, copper (II) carbonate, copper (II) diphosphate, copper (II) iodide, copper (II) fluoride, copper (II) sulfate, copper (II) phosphate, and copper (II) nitrate; copper (I) salts, e.g., copper (I) bromide, copper (I) chloride, copper (I) iodide, and copper (I) thiocyanate; and nickel salts, e.g., nickel (II) acetate, nickel (II) formate, nickel (II) bromide, nickel (II) carbonate, nickel (II) chloride, nickel (II) nitrate, and nickel (II) sulfate.

The amount of transition metal ion or salt added is generally from 0.01 to 10.0 mM (preferably, 0.1 to 1.0 mM) per mM of the L-γ-glutamyl-3-carboxy-4-nitroanilide or a salt thereof. In smaller amounts than the above, instances of non-enzymatic hydrolysis of the substrate may occur whereas when used in greater amounts, the transition metal ion or salt tends to inhibit γ-GTP activity.

In order to obtain a substantial stabilizing effect on the substrate, the substrate-containing buffer solution to which a transition metal ion or salt is to be added is preferably maintained at a pH of from 4.0 to 8.0, and more preferably from 5.0 to 7.0. Usable buffers are not particularly limited as long as they are capable of maintaining a pH within the above range. Such buffers include those having no chelating properties. Illustrative examples include Good's buffers, such as 2-(N-morpholino)ethanesulfonic acid (abbreviated as MES), Piperazine-N,N'-bis(2-ethanesulfonic acid) (abbreviated as PIPES), N-(2-acetamido)-2-aminoethanesulfonic acid (abbreviated as ACES), N,N-bis(2-hydroxyethyl)-2-aminoethanesulfonic acid (abbreviated as BES), bis(2-hydroxyethyl)iminotris(hydroxymethyl)methane (abbreviated as Bis-tris), 3-[N,N-bis(2-hydroxyethyl)amino]-2-hydroxypropanesulfonic acid (abbreviated as DIPSO), N-2-hydroxyethylpiperazine-N'- 3-propanesulfonic acid (abbreviated as EPPS), N-2-hydroxyethylpiperazine-N'-2-ethanesulfonic acid (abbreviated as HEPES), N-2-hydroxyethylpiperazine-N'-2-hydroxypropane- 3-sulfonic acid (abbreviated as HEPPSO), 3-(N-morpholino)propanesulfonic acid (abbreviated as MOPS), 3-(N-morpholino)-2-hydroxypropanesulfonic acid (abbreviated as MOPSO), piperazine-N,N'-bis(2-hydroxypropanesulfonic acid (abbreviated as POPSO), N-tris(hydroxymethyl)methyl-3-aminopropanesulfonic acid (abbreviated as TAPS), N-tris(hydroxymethyl)methyl- 2-hydroxy-3-aminopropanesulfonic acid (abbreviated as TAPSO), and N-tris(hydroxymethyl)methyl- 2-aminoethanesulfonic acid (abbreviated as TES); 2-amino-2-hydroxymethyl- 1,3-propanediol (also called tris(hydroxymethyl)aminomethane; referred to as "Tris" hereinafter); and phosphate buffer solutions. Among these buffers, MES, Bis-tris, ACES, PIPES, and MOPS are preferably for the present invention, and MES is the most preferable. The amount of the buffer is not particularly limited as far as the stable pH is maintained for a long time (generally from 10 to 200 mM).

The reagent for determining γ-glutamyl transpeptidase activity according to the present invention can be provided in a state of solution as well as a freezed state or a freeze-dried state. In a freeze-dried state, the reagent may further contain excipients such as sugars (e.g., sucrose and lactose).

In the present invention, a transition metal ion or salt prevents non-enzymatic hydrolysis of the substrate so that a chelating agent as hereinafter described is not an essential component. However, reduction in γ-GTP measured values ascribable to transition metal ion or salt are observed in some samples. Although the influence of the transition metal ion or salt is slight as compared with non-enzymatic hydrolysis of the substrate, it is possible to avoid such influence by using a chelating agent as a precautionary measure.

The chelating agent, if used, must be present during the enzymatic reaction so that it may previously be added to liquid B. When it is added to liquid A, i.e., a buffer solution containing the substrate and a transition metal ion or salt, care should be taken because the chelating agent sometimes hinders the action of the transition metal ion or salt during storage. The chelating agent is suitably added in an effective amount such as an amount of from about 1 to 100 mM per mM (final concentration) of the transition metal ion or salt. The preferable amount of the chelating agent changes depending on the type of the transition metal. For example, the chelating agent is used preferably in an amount of from 1 to 20 mM when Cu (II) or Cu (I) is used. Addition of larger amounts of a chelating agent makes no difference in the effect, it only increases the cost.

Illustrative examples of suitable chelating agents to be used in the present invention include ethylenediamine-N,N,N',N'-tetraacetic acid (abbreviated as EDTA), 1,2-cyclohexanediamine-N,N,N',N'-tetraacetic acid (abbreviated as CyDTA), glycol ether diamine-N,N,N',N'-tetraacetic acid (abbreviated as GEDTA), hexamethylenediamine-N,N,N',N'-tetraacetic acid (abbreviated as HDTA), hydroxyethyliminodiacetic acid (abbreviated as HIDA), 1,3-diaminopropan- 2-ol-N,N,N',N'-tetraacetic acid (abbreviated as DPTA-OH), diethylenetriamine-N,N,N',N'',N''-pentaacetic acid (abbreviated as DTPA), ethylenediamine-N,N'-diacetic acid (abbreviated as EDDA), ethylenediamine-N,N'-dipropionic acid (abbreviated as EDDP), N-hydroxyethylethylenediamine-N,N',N'-triacetic acid (abbreviated as EDTA-OH), and 1,2-diaminopropane-N,N,N', N'-tetraacetic acid (abbreviated as Methyl-EDTA), and salts of these acids.

The reagent of the present invention may further contain other additives such as surfactants, preservatives, and the like.

The reagent of the present invention should be composed of at least two-parts and the reagent composed of two-parts is preferable. The transition metal ion or salt should coexist with the substrate. However, the amino acid or peptide should not coexist with the substrate before use and the chelating agent should not coexist with the transition metal ion or salt before use.

According to the present invention, γ-GTP activity can be measured using the above-mentioned reagent in a known manner (cf. JP-A-49-86338 or JP-B-54-7781 corresponding to U.S. Pat. Nos. 3,979,447, 3,986,931 and 4,049,702) (the term "JP-B" as used herein means an "examined Japanese patent publication"), and *Clinica Chimica Acta*, 315F-338F (1983), herein incorporated by reference). That is, 3-carboxy-4-nitroaniline, which is released from the substrate by the enzymatic action of γ-GTP, is directly measured by colorimetry at a wavelength of around 410 nm.

The transition metal ion or salt, such as a copper or nickel ion or salt, functions to increase stability of L-γ-glutamyl-3-carboxy-4-nitroanilide or its salt in an aqueous solution thereby prevents non-enzymatic hydrolysis. While the mechanism of action of the transition metal ion or salt is not clear, it is assumed that a transition metal ion and L-γ-glutamyl-3-carboxy-4-nitroanilide form a chelate-like compound which is less susceptible to non-enzymatic hydrolysis. The inventor has experimentally confirmed that copper (both (II) and (I)) and the substrate form a complex having a substrate to copper ratio of 4:1.

The chelating agent used in combination functions to prevent adverse influences of the transition metal ion or salt added to the reagent. Where a transition metal ion or salt is added to a buffer solution containing L-γ-glutamyl-3-carboxy- 4-nitroanilide, slight interference with γ-GTP activity by the transition metal ion or salt is observed in some cases depending on a sample to be assayed. Such inhibition of γ-GTP activity can be avoided by the presence of a chelating agent in the γ-GTP enzymatic reaction system.

The present invention will now be illustrated in greater detail with reference to the following Examples, but the present invention should not be construed as being limited thereto.

EXAMPLE 1

Effect of the Transition Metal Ion or Salt to Prevent Non-enzymatic Hydrolysis of L-γ-glutamyl-3-carboxy-4-nitroanilide The effect of copper (II) chloride ($CuCl_2$), copper (II) sulfate ($CuSO_4$), copper (II) nitrate ($Cu(NO_3)_2$), nickel (II) chloride ($NiCl_2$) or nickel (II) sulfate ($NiSO_4$) to prevent non-enzymatic hydrolysis of L-γ-glutamyl-3-carboxy-4-nitroanilide was examined as follows.

Liquids A and B having the following compositions were prepared and stored at 25° C. for 1 or 2 weeks.

| Liquid A: | |
|---|---|
| MES buffer solution (pH = 6.0) | 20 mM |
| L-γ-Glutamyl-3-carboxy-4-nitroanilide | 7.50 mM |
| Additive shown in Table 1 | see Table 1 |
| Liquid B: | |
| Glycylglycine buffer solution (pH = 8.2) | 750 mM |
| EDTA · 2Na | 50 mM |

To 2.0 ml of liquid A was added 0.5 ml of liquid B, followed by stirring, and the absorbance at 404 nm was measured to trace the optical change of the reagent per se, which serves as a blank in actual assays. For comparison, a reagent of the same composition, except for containing no transition metal ion or salt, was used. The results obtained are shown in Table 1 below. Tables 2 and 3 show relative absorbances measuring the absorbance immediately after preparation of the reagent (storage time: 0 week) as 100% and increases in absorbance with time, respectively.

TABLE 1

| | Absorbance at 404 nm | | | | | |
|---|---|---|---|---|---|---|
| Storage Time (week) | No Addition | $CuCl_2$ 3.0 mM | $CuSO_4$ 3.0 mM | $Cu(NO_3)_2$ 3.0 mM | $NiCl_2$ 3.75 mM | $NiSO_4$ 3.75 mM |
| 0 | 0.6884 | 0.6886 | 0.6869 | 0.6844 | 0.6943 | 0.6883 |
| 1 | 0.9354 | 0.7483 | 0.7453 | 0.7468 | 0.8760 | 0.8773 |
| 2 | 1.0173 | 0.8060 | 0.8018 | 0.8039 | 0.9347 | 0.9387 |

TABLE 2

| | Relative Absorbance (%) at 404 nm | | | | | |
|---|---|---|---|---|---|---|
| Storage Time (week) | No Addition | $CuCl_2$ 3.0 mM | $CuSO_4$ 3.0 mM | $Cu(NO_3)_2$ 3.0 mM | $NiCl_2$ 3.75 mM | $NiSO_4$ 3.75 mM |
| 0 | 100.0 | 100.0 | 100.0 | 100.0 | 100.0 | 100.0 |
| 1 | 135.9 | 108.7 | 108.5 | 109.1 | 126.2 | 127.5 |
| 2 | 147.8 | 117.0 | 116.7 | 117.5 | 134.6 | 136.4 |

TABLE 3

| | Increase in Absorbance at 404 nm | | | | | |
|---|---|---|---|---|---|---|
| Storage Time (week) | No Addition | $CuCl_2$ 3.0 mM | $CuSO_4$ 3.0 mM | $Cu(NO_3)_2$ 3.0 mM | $NiCl_2$ 3.75 mM | $NiSO_4$ 3.75 mM |
| 1 | 0.2470 | 0.0597 | 0.0584 | 0.0624 | 0.1817 | 0.1890 |
| 2 | 0.3289 | 0.1174 | 0.1149 | 0.1195 | 0.2404 | 0.2504 |

Tables 1 to 3 show that non-enzymatic hydrolysis of the substrate is effectively inhibited in each case as compared with the reagent containing no additive. No substantial difference in effect was observed between copper salts and nickel salts or among the various kinds of salts.

EXAMPLE 2

Effect of the Transition Metal Ion or Salt to Prevent Non-enzymatic Hydrolysis of L-γ-glutamyl-3-carboxy-4-nitroanilide The effect of copper (II) chloride ($CuCl_2$) or nickel (II) chloride ($NiCl_2$) to prevent non-enzymatic hydrolysis of L-γ-glutamyl-3-carboxy-4-nitroanilide was examined in comparison with additives known to have a stabilizing effect on L-γ-glutamyl-4-nitroanilide, i.e., 15-crown-5, 12-crown-4, and β-cyclodextrin.

Liquids A and B having the following compositions were prepared and stored at 25° C. for 1, 2 or 7 weeks.

| Liquid A: | |
|---|---|
| MES buffer solution (pH = 6.0) | 20 mM |
| L-γ-Glutamyl-3-carboxy-4-nitroanilide | 7.50 mM |
| Additive shown in Table 4 below | see Table 4 |
| Liquid B: | |
| Glycylglycine buffer solution (pH = 8.2) | 750 mM |
| EDTA · 2Na | 50 mM |

The absorbance of a mixture of liquid A and liquid B at 404 nm was measured in the same manner as in Example 1. The results obtained are shown in Tables 4 to 6.

TABLE 4

| | Absorbance at 404 nm | | | | | |
|---|---|---|---|---|---|---|
| Storage Time (week) | No Addition | $CuCl_2$ 3.0 mM | $NiCl_2$ 10 mM | 15-Crown-5 10 mM | 12-Crown-4 10 mM | β-Cyclodextrin 1.0% (w/v) |
| 0 | 0.6900 | 0.6962 | 0.7316 | 0.6913 | 0.6885 | 0.6919 |
| 1 | 0.8576 | 0.7531 | 0.8298 | 0.8541 | 0.8515 | 0.8556 |
| 2 | 1.0292 | 0.8064 | 0.9353 | 1.0240 | 1.0168 | 1.0244 |
| 7 | 1.8953 | 1.0745 | — | — | — | — |

TABLE 5

| | Relative Absorbance (%) at 404 nm | | | | | |
|---|---|---|---|---|---|---|
| Storage Time (week) | No Addition | $CuCl_2$ 3.0 mM | $NiCl_2$ 10 mM | 15-Crown-5 10 mM | 12-Crown-4 10 mM | β-Cyclodextrin 1.0% (w/v) |
| 0 | 100.0 | 100.0 | 100.0 | 100.0 | 100.0 | 100.0 |
| 1 | 124.3 | 108.2 | 113.4 | 123.5 | 123.7 | 123.7 |

TABLE 5-continued

Relative Absorbance (%) at 404 nm

| Storage Time (week) | No Addition | CuCl$_2$ 3.0 mM | NiCl$_2$ 10 mM | 15-Crown-5 10 mM | 12-Crown-4 10 mM | β-Cyclodextrin 1.0% (w/v) |
|---|---|---|---|---|---|---|
| 2 | 149.2 | 115.8 | 127.8 | 148.2 | 147.7 | 148.1 |
| 7 | 274.7 | 154.3 | — | — | — | — |

TABLE 6

Increase in Absorbance at 404 nm

| Storage Time (week) | No Addition | CuCl$_2$ 3.0 mM | NiCl$_2$ 10 mM | 15-Crown-5 10 mM | 12-Crown-4 10 mM | β-Cyclodextrin 1.0% (w/v) |
|---|---|---|---|---|---|---|
| 1 | 0.1676 | 0.0569 | 0.0982 | 0.1628 | 0.1630 | 0.1637 |
| 2 | 0.3392 | 0.1102 | 0.2037 | 0.3327 | 0.3283 | 0.3325 |
| 7 | 1.2053 | 0.3783 | — | — | — | — |

Tables 4 to 6 show that the known additives which are thought to prevent non-enzymatic hydrolysis of L-γ-glutamyl-4-nitroanilide are not effective on L-γ-glutamyl-3-carboxy-4-nitroanilide.

EXAMPLE 3

Effect of the Transition Metal Ion or Salt to Prevent Non-enzymatic Hydrolysis of L-γ-glutamyl-3-carboxy-4-nitroanilide (3).

The effect of copper (I) chloride (CuCl) on the inhibition of non-enzymatic hydrolysis of L-γ-glutamyl-3-carboxy-4-nitroanilide was examined as follows.

Liquids A and B having the following compositions were prepared and stored at 25° C. for 1, 2, 3 or 4 weeks.

| Liquid A: | |
|---|---|
| MES buffer solution (pH = 6.0) | 20 mM |
| L-γ-Glutamyl-3-carboxy-4-nitroanilide | 7.50 mM |
| CuCl | see Table 7 |
| Liquid B: | |
| Glycylglycine buffer solution (pH = 8.2) | 750 mM |
| EDTA · 2Na | 20 mM |

The absorbance of a mixture of liquid A and liquid B at 404 nm was measured in the same manner as in Example 1. The results obtained are shown in Tables 7 to 9.

TABLE 7

Absorbance at 404 nm

| Storage Time (week) | No Addition | CuCl 1.875 mM | CuCl 2.50 mM | CuCl 3.75 mM | CuCl 7.50 mM |
|---|---|---|---|---|---|
| 0 | 0.6884 | 0.7580 | 0.8043 | 0.8912 | 1.0599 |
| 1 | 0.8449 | 0.8866 | 0.9220 | 0.9752 | 1.1049 |
| 2 | 1.0165 | 1.0134 | 1.0234 | 1.0514 | 1.1265 |
| 3 | 1.1604 | 1.1141 | 1.1357 | 1.1353 | 1.1623 |
| 4 | 1.3440 | 1.2542 | 1.2424 | 1.2171 | 1.1908 |

TABLE 8

Relative Absorbance (%)

| Storage Time (week) | No Addition | CuCl 1.875 mM | CuCl 2.50 mM | CuCl 3.75 mM | CuCl 7.50 mM |
|---|---|---|---|---|---|
| 0 | 100.0 | 100.0 | 100.0 | 100.0 | 100.0 |
| 1 | 122.7 | 117.0 | 114.6 | 109.4 | 104.2 |
| 2 | 147.7 | 133.7 | 127.2 | 118.0 | 106.3 |
| 3 | 168.6 | 147.0 | 141.2 | 127.4 | 109.7 |
| 4 | 195.2 | 165.5 | 154.6 | 136.6 | 112.4 |

TABLE 9

Increase in Absorbance at 404 nm

| Storage Time (week) | No Addition | CuCl 1.875 mM | CuCl 2.50 mM | CuCl 3.75 mM | CuCl 7.50 mM |
|---|---|---|---|---|---|
| 1 | 0.1565 | 0.1287 | 0.1178 | 0.0841 | 0.0450 |
| 2 | 0.3281 | 0.2554 | 0.2192 | 0.1603 | 0.0666 |
| 3 | 0.4720 | 0.3561 | 0.3314 | 0.2441 | 0.1024 |
| 4 | 0.6556 | 0.4962 | 0.4392 | 0.3260 | 0.1309 |

Tables 7 to 9 demonstrate that non-enzymatic hydrolysis of the substrate is effectively prevented in the reagent containing copper (I) chloride as compared with the reagent containing no additive.

EXAMPLE 4

Storage Stability of the Substrate Solution Containing a Transition Metal Ion or Salt The stabilizing effect of a transition metal ion or salt on a substrate solution was examined as follows using CuCl$_2$.

Liquids A and B having the following compositions were prepared and stored at 25° C. for 7 weeks.

| Liquid A: | |
|---|---|
| MES buffer solution (pH = 6.0) | 20 mM |
| L-γ-Glutamyl-3-carboxy-4-nitroanilide | 7.50 mM |
| CuCl$_2$ | 0 or 3.0 mM |
| Liquid B: | |
| Glycylglycine buffer solution (pH = 8.2) | 750 mM |
| EDTA · 2Na | 20 mM |

To 300 μl of liquid A was added 10 μl of a serum sample to be assayed, and the mixture was preincubated at 37° C. for 5 minutes. To the mixture was added 75 μl of liquid B, followed by stirring. A γ-GTP value (IU/l) of each sample was obtained from the rate of increase of absorbance with time at a main wavelength of 404 nm and a secondary wavelength of 500 nm based on the rate of increase of absorbance of an enzyme solution having a known γ-GTP value. The measurements were made with an automatic analyzer "TBA-30R" manufactured by Toshiba. The results obtained are shown in Tables 10 to 12.

TABLE 10

γ-GTP Activity (IU/l)

| Serum Sample No. | No Addition | | CuCl$_2$ Added | |
|---|---|---|---|---|
| | Immediately After Preparation | After Preservation at 25° C. × 7 Wks | Immediately After Preparation | After Preservation at 25° C. × 7 Wks |
| 1 | 21 | 20 | 21 | 21 |
| 2 | 67 | 63 | 67 | 66 |
| 3 | 191 | 177 | 189 | 187 |
| 4 | 120 | 110 | 119 | 117 |
| 5 | 262 | 244 | 260 | 257 |
| 6 | 37 | 30 | 37 | 36 |
| 7 | 136 | 125 | 136 | 133 |
| 8 | 215 | 199 | 212 | 210 |
| 9 | 257 | 239 | 255 | 251 |

TABLE 11

Relative γ-GTP Activity (%) Based on Non-Addition System Immediately After Preparation

| Serum Sample No. | No Addition | | CuCl$_2$ Added | |
|---|---|---|---|---|
| | Immediately After Preparation | After Preservation at 25° C. × 7 Wks | Immediately After Preparation | After Preservation at 25° C. × 7 Wks |
| 1 | 100.0 | 95.2 | 100.0 | 100.0 |
| 2 | 100.0 | 94.0 | 100.0 | 98.5 |
| 3 | 100.0 | 92.7 | 99.0 | 97.9 |
| 4 | 100.0 | 91.7 | 99.2 | 97.5 |
| 5 | 100.0 | 93.1 | 99.2 | 98.1 |
| 6 | 100.0 | 81.1 | 100.0 | 97.3 |
| 7 | 100.0 | 91.9 | 100.0 | 97.8 |
| 8 | 100.0 | 92.6 | 98.6 | 97.7 |
| 9 | 100.0 | 93.0 | 99.2 | 97.7 |

TABLE 12

Relative γ-GTP Activity (%) Based on CuCl$_2$-Added System Immediately After Preparation

| Serum Sample No. | No Addition | | CuCl$_2$ Added | |
|---|---|---|---|---|
| | Immediately After Preparation | After Preservation at 25° C. × 7 Wks | Immediately After Preparation | After Preservation at 25° C. × 7 Wks |
| 1 | | | 100.0 | 100.0 |
| 2 | | | 100.0 | 98.5 |
| 3 | | | 100.0 | 98.9 |
| 4 | | | 100.0 | 98.3 |
| 5 | | | 100.0 | 98.8 |
| 6 | | | 100.0 | 97.3 |
| 7 | | | 100.0 | 97.8 |
| 8 | | | 100.0 | 99.1 |
| 9 | | | 100.0 | 98.4 |

As is shown in Tables 10 to 12, the γ-GTP values obtained using a CuCl$_2$-containing substrate solution having been preserved at 25° C. for 7 weeks correspond to 97.3% to 100.0% of those obtained by using a substrate solution free of CuCl$_2$ measured immediately after preparation. Similarly, these results correspond to 97.3% to 100.0% of those obtained by using a CuCl$_2$-containing substrate solution immediately after preparation, demonstrating that the CuCl$_2$-containing substrate solution exhibits no substantial reduction in γ-GTP measured values. To the contrary, the γ-GTP values obtained using a substrate solution free from CuCl$_2$ and having been preserved at 25° C. for 7 weeks correspond to only 81.1% to 95.2% of those obtained by using a substrate solution free of CuCl$_2$ measured immediately after the preparation, revealing a reduction of about 5 to 20% in γ-GTP measured value.

EXAMPLE 5

Effect of the Chelating Agent on Exclusion of Adverse Influences of a Transition Metal Ion Adverse influences of a transition metal ion on a γ-GTP determination system and the effect of a chelating agent on exclusion of such influences were examined as follows.

A γ-GTP value of serum samples was measured in the same manner as in Example 4 using liquids A and B having the following compositions. The results obtained are shown in Tables 13 to 16 below.

| Liquid A: | |
|---|---|
| MES buffer solution (pH = 6.0) | 20 mM |
| L-γ-Glutamyl-3-carboxy-4-nitroanilide | 7.50 mM |
| Additive: | |
| CuCl$_2$ | 0 or 3.0 mM |
| or | |
| NiCl$_2$ | 0 or 1.25 mM |
| Liquid B: | |
| Glycylglycine buffer solution (pH = 8.2) | 750 mM |
| EDTA · 2Na | 0 or 20 or 50 mM |

TABLE 13

γ-GTP Activity (IU/l)

| Sample | No EDTA Added | | 20 mM EDTA Added | |
|---|---|---|---|---|
| Serum No. | No CuCl$_2$ Added | CuCl$_2$ 3.0 mM | No CuCl$_2$ Added | CuCl$_2$ 3.0 mM |
| 1 | 23 | 22 | 23 | 23 |
| 2 | 18 | 17 | 18 | 18 |
| 3 | 34 | 33 | 34 | 34 |
| 4 | 130 | 129 | 130 | 130 |
| 5 | 54 | 53 | 55 | 54 |
| 6 | 165 | 161 | 164 | 163 |
| 7 | 76 | 75 | 76 | 76 |
| 8 | 115 | 113 | 115 | 115 |
| 9 | 184 | 183 | 184 | 184 |
| 10 | 454 | 451 | 453 | 451 |

TABLE 14

Relative γ-GTP Activity (%) Based on Non-Addition System

| Sample | No EDTA Added | | 20 mM EDTA Added | |
|---|---|---|---|---|
| Serum No. | No CuCl$_2$ Added | CuCl$_2$ 3.0 mM | No CuCl$_2$ Added | CuCl$_2$ 3.0 mM |
| 1 | 100.0 | 95.6 | 100.0 | 100.0 |
| 2 | 100.0 | 94.4 | 100.0 | 100.0 |
| 3 | 100.0 | 97.1 | 100.0 | 100.0 |
| 4 | 100.0 | 99.2 | 100.0 | 100.0 |
| 5 | 100.0 | 98.1 | 101.9 | 100.0 |
| 6 | 100.0 | 97.6 | 99.4 | 98.8 |
| 7 | 100.0 | 98.7 | 100.0 | 100.0 |
| 8 | 100.0 | 98.2 | 100.0 | 100.0 |
| 9 | 100.0 | 99.5 | 100.0 | 100.0 |
| 10 | 100.0 | 99.3 | 99.8 | 99.3 |

TABLE 15

γ-GTP Activity (IU/l)

| Sample | No EDTA Added | | 50 mM EDTA Added | |
|---|---|---|---|---|
| Serum No. | No NiCl$_2$ Added | NiCl$_2$ 1.25 mM | No NiCl$_2$ Added | NiCl$_2$ 1.25 mM |
| 1 | 120 | 115 | 119 | 120 |
| 2 | 39 | 37 | 39 | 39 |
| 3 | 18 | 17 | 18 | 18 |
| 4 | 58 | 56 | 59 | 58 |
| 5 | 211 | 203 | 210 | 210 |
| 6 | 640 | 607 | 633 | 635 |

TABLE 16

Relative γ-GTP Activity (%) Based on Non-Addition System

| Sample | No EDTA Added | | 50 mM EDTA Added | |
|---|---|---|---|---|
| Serum No. | No NiCl$_2$ Added | NiCl$_2$ 1.25 mM | No NiCl$_2$ Added | NiCl$_2$ 1.25 mM |
| 1 | 100.0 | 95.8 | 99.2 | 100.0 |
| 2 | 100.0 | 94.9 | 100.0 | 100.0 |
| 3 | 100.0 | 94.4 | 100.0 | 100.0 |
| 4 | 100.0 | 96.6 | 101.7 | 100.0 |
| 5 | 100.0 | 96.2 | 99.5 | 99.5 |
| 6 | 100.0 | 94.8 | 98.9 | 99.2 |

Depending on samples, the γ-GTP value as measured using a substrate solution containing a copper salt or a nickel salt sometimes become slightly lower than that measured by a substrate solution containing no transition metal ion or salt. Such a tendency can be eliminated by the addition of a chelating agent to liquid B to obtain a measured value equal to that obtained using a reagent containing no transition metal ion or salt. When a chelating agent is added to liquid B while adding no transition metal ion or salt to liquid A, no change occurs in measured value, indicating that the chelating agent itself has no influence.

EXAMPLE 6

Comparison of Effect Among Various Chelating Agents

The effect of various chelating agents on a substrate solution containing CuCl$_2$ was examined as follows.

A γ-GTP value of serum samples was measured in the same manner as in Example 4 using liquids A and B having the following compositions. The results obtained are shown in Tables 17 and 18 below.

Liquid A:

| | |
|---|---|
| MES buffer solution (pH = 6.0) | 20 mM |
| L-γ-Glutamyl-3-carboxy-4-nitroanilide | 7.50 mM |
| CuCl$_2$ | 0 or 3.0 mM |

Liquid B:

| | |
|---|---|
| Glycylglycine buffer solution (pH = 8.2) | 750 mM |
| EDTA · 2Na, CyDTA, EDDP · HCl, or GEDTA | 0 or 20 mM |

TABLE 17

γ-GTP Value (IU/l)

| | | 3.0 mM CuCl$_2$ Added | | | | |
|---|---|---|---|---|---|---|
| Sample Serum No. | No Addition | No Chelating Agent Added | EDTA 20 mM | CyDTA 20 mM | EDDP 20 mM | GEDTA 20 mM |
| 1 | 120 | 117 | 120 | 121 | 120 | 120 |
| 2 | 39 | 38 | 39 | 39 | 39 | 39 |
| 3 | 18 | 17 | 18 | 18 | 18 | 18 |
| 4 | 10 | 10 | 10 | 10 | 10 | 10 |
| 5 | 58 | 57 | 57 | 58 | 57 | 58 |
| 6 | 58 | 58 | 58 | 58 | 58 | 58 |
| 7 | 95 | 90 | 95 | 94 | 95 | 95 |
| 8 | 143 | 137 | 143 | 143 | 143 | 143 |
| 9 | 211 | 204 | 210 | 209 | 210 | 210 |
| 10 | 640 | 607 | 635 | 637 | 637 | 636 |

TABLE 18

Relative γ-GTP Value (%) Based on No Addition System

| | | 3.0 mM CuCl$_2$ Added | | | | |
|---|---|---|---|---|---|---|
| Sample Serum No. | No Addition | No Chelating Agent Added | EDTA 20 mM | CyDTA 20 mM | EDDP 20 mM | GEDTA 20 mM |
| 1 | 100.0 | 97.5 | 100.0 | 100.8 | 100.0 | 100.0 |
| 2 | 100.0 | 97.4 | 100.0 | 100.0 | 100.0 | 100.0 |
| 3 | 100.0 | 94.4 | 100.0 | 100.0 | 100.0 | 100.0 |
| 4 | 100.0 | 100.0 | 100.0 | 100.0 | 100.0 | 100.0 |
| 5 | 100.0 | 98.3 | 98.3 | 100.0 | 98.3 | 100.0 |
| 6 | 100.0 | 100.0 | 100.0 | 100.0 | 100.0 | 100.0 |
| 7 | 100.0 | 94.7 | 100.0 | 98.9 | 100.0 | 100.0 |
| 8 | 100.0 | 95.8 | 100.0 | 100.0 | 100.0 | 100.0 |
| 9 | 100.0 | 96.7 | 99.5 | 99.1 | 100.0 | 100.0 |

TABLE 18-continued

Relative γ-GTP Value (%) Based on No Addition System

| | | 3.0 mM CuCl$_2$ Added | | | | |
|---|---|---|---|---|---|---|
| Sample Serum No. | No Addition | No. Chelating Agent Added | EDTA 20 mM | CyDTA 20 mM | EDDP 20 mM | GEDTA 20 mM |
| 10 | 100.0 | 94.8 | 99.2 | 99.5 | 99.5 | 99.4 |

As is apparent from Tables 17 and 18, the γ-GTP values as measured using a CuCl$_2$-containing substrate solution are approximately equal to those obtained using a substrate solution containing no transition metal ion or salt by adding a chelating agent of various kinds to the substrate solution. No difference was observed among the various chelating agents.

EXAMPLE 7

Comparison of Effect Among Various Salts of the Transition Metal

Influences of the type of salt on a γ-GTP determination system were examined as follows using CuCl$_2$, CuSO$_4$, and Cu(NO$_3$)$_2$.

A γ-GTP value of serum samples was measured in the same manner as in Example 4 using liquids A and B having the following compositions. The results obtained are shown in Tables 19 and 20 below.

| Liquid A: | |
|---|---|
| MES buffer solution (pH = 6.0) | 20 mM |
| L-γ-Glutamyl-3-carboxy-4-nitroanilide | 7.50 mM |
| Copper salt shown in Table 19 | 0 or 3.0 mM |
| Liquid B: | |
| Glycylglycine buffer solution (pH = 8.2) | 750 mM |
| EDTA · 2Na | 20 mM |

TABLE 19

γ-GTP Value (IU/l)

| Sample Serum No. | No Addition | CuCl$_2$ 3.0 mM | CuSO$_4$ 3.0 mM | Cu(NO$_3$)$_2$ 3.0 mM |
|---|---|---|---|---|
| 1 | 69 | 69 | 69 | 69 |
| 2 | 71 | 71 | 71 | 71 |
| 3 | 105 | 106 | 106 | 106 |
| 4 | 73 | 72 | 73 | 72 |
| 5 | 26 | 26 | 26 | 26 |
| 6 | 1686 | 1660 | 1663 | 1658 |
| 7 | 266 | 266 | 266 | 266 |
| 8 | 140 | 138 | 138 | 139 |
| 9 | 21 | 21 | 21 | 21 |
| 10 | 50 | 50 | 50 | 50 |

TABLE 20

Relative γ-GTP Value (%) Based on No Copper Salt System

| Sample Serum No. | No Addition | CuCl$_2$ 3.0 mM | CuSO$_4$ 3.0 mM | Cu(NO$_3$)$_2$ 3.0 mM |
|---|---|---|---|---|
| 1 | 100.0 | 100.0 | 100.0 | 100.0 |
| 2 | 100.0 | 100.0 | 100.0 | 100.0 |
| 3 | 100.0 | 101.0 | 101.0 | 101.0 |
| 4 | 100.0 | 98.6 | 100.0 | 98.6 |
| 5 | 100.0 | 100.0 | 100.0 | 100.0 |
| 6 | 100.0 | 98.5 | 98.6 | 98.3 |
| 7 | 100.0 | 100.0 | 100.0 | 100.0 |
| 8 | 100.0 | 98.6 | 98.6 | 99.3 |
| 9 | 100.0 | 100.0 | 100.0 | 100.0 |
| 10 | 100.0 | 100.0 | 100.0 | 100.0 |

As can be seen from the results in Tables 19 and 20, the γ-GTP values obtained using a copper salt-containing substrate solution fall within a range of from 98.3 to 101.0% of those obtained using a substrate solution containing no copper salt, and no difference was found among the various copper salts, thus confirming the equal usefulness of these copper salts.

As described and demonstrated above, non-enzymatic hydrolysis of L-γ-glutamyl-3-carboxy-4-nitroanilide in a solution can be effectively prevented by the addition of a transition metal ion or salt, such as a copper salt or a nickel salt, to the solution. The present invention thus makes it possible to utilize L-γ-glutamyl-3-carboxy-4-nitroanilide as a substrate having excellent preservability as well as high solubility.

Accordingly, the reagent suitable for γ-GTP activity determination of the present invention can be supplied as a solution. Even when supplied as a freeze-dried product, the reagent is very easy to use due to its excellent preservability after being dissolved as needed.

In cases where the transition metal ion or salt, while exhibiting excellent activity to prevent non-enzymatic hydrolysis of the substrate, furnishes somewhat lower γ-GTP values, sufficient precision is guaranteed by the presence of a chelating agent at the time of the γ-GTP enzyme reaction. In other words, the presence of a chelating agent in the enzyme reaction system completely excludes adverse influences of the transition metal ion or salt added.

The present invention thus makes it feasible to supply a storage-stable reagent for γ-GTP determination in a solution which can be used as supplied without preparation. By contrast, conventional reagents must be supplied in a dry state and the amount required for each clinical examination must be dissolved at the time of use, thus the reagent solution provided by the present invention is of great advantage from the economical viewpoint.

While the invention has been described in detail and with reference to specific examples, it will be apparent to one skilled in the art that various changes and modifications can be made without departing from the spirit and scope of the invention.

What is claimed is:

1. A reagent for determining γ-glutamyl transpeptidase activity in a test sample comprising L-γ-glutamyl-3-carboxy-4-nitroanilide or a salt thereof as a substrate and a transition metal ion or salt.

2. A reagent for determining γ-glutamyl transpeptidase activity in a test sample comprising:

component A comprising L-γ-glutamyl-3-carboxy-4-nitroanilide or a salt thereof as a substrate, a transition metal ion or salt as a stabilizer and a buffer material, and component B comprising an amino acid or peptide as a recipient of a γ-glutamyl group and a buffer material.

3. The reagent of claim 1 or 2, wherein said transition metal is copper.

4. The reagent of claim 3, wherein said transition metal is copper (I).

5. The reagent of claim 3, wherein said transition metal is copper (II).

6. The reagent of claim 1 or 2, wherein said transition metal is nickel.

7. The reagent of claim 1 or 2, wherein said transition metal salt is selected from the group consisting of copper (II) acetate, copper (II) citrate, copper (II) formate, copper (II) gluconate, copper (II) oleate, copper (II) oxalate, copper (II) phthalate, copper (II) bromide, copper (II) chloride, copper (II) carbonate, copper (II) diphosphate, copper (II) iodide, copper (II) fluoride, copper (II) sulfate, copper (II) phosphate, copper (II) nitrate, copper (I) bromide, copper (I) chloride, copper (I) iodide, copper (I) thiocyanate, nickel (II) acetate, nickel (II) formate, nickel (II) bromide, nickel (II) carbonate, nickel (II) chloride, nickel (II) nitrate, and nickel (II) sulfate.

8. The reagent of claim 1 or 2, wherein said transition metal is present in an amount of from 0.01 to 10.0 mM per mM of the substrate.

9. The reagent of claim 8, wherein said transition metal is present in an amount of from 0.1 to 1.0 mM per mM of the substrate.

10. The reagent of claim 1 or 2, wherein said reagent is an aqueous solution.

11. In a reagent for determining γ-glutamyl transpeptidase activity in a test sample comprising L-γ-glutamyl-3-carboxy-4-nitroanilide or a salt thereof as a substrate, the improvement wherein said L-γ-glutamyl-3-carboxy-4-nitroanilide or a salt thereof is stabilized by the presence of a transition metal ion or salt.

12. A method for stabilizing L-γ-glutamyl-3-carboxy-4-nitroanilide or a salt thereof comprising adding a transition metal ion or salt to the L-γ-glutamyl-3-carboxyl-4-nitroanilide or a salt thereof.

13. The method of claim 12, wherein said transition metal is copper.

14. The method of claim 13, wherein said transition metal is copper (I).

15. The method of claim 13, wherein said transition metal is copper (II).

16. The method of claim 12, wherein said transition metal is nickel.

17. The method of any one of claims 12 to 16, wherein said L-γ-glutamyl-3-carboxyl-4-nitroanilide or a salt thereof exists in a solution.

18. A method for determining γ-glutamyl transpeptidase activity in a test sample comprising:

mixing a test sample with component A and component B in any order, wherein said component A comprises L-γ-glutamyl- 3-carboxy-4-nitroanilide or a salt thereof as a substrate, a transition metal ion or salt as a stabilizer and a buffer material and wherein component B comprises an amino acid or peptide as a recipient of a γ-glutamyl group and a buffer material, measuring a rate of increase of 3-carboxy-4-nitroaniline released from the substrate, and determining the γ-glutamyl transpeptidase activity in the test sample based on the rate of increase of 3-carboxy-4-nitroaniline.

19. The method of claim 18, wherein said transition metal is copper.

20. The method of claim 19, wherein said transition metal is copper (I).

21. The method of claim 19, wherein said transition metal is copper (II).

22. The method of claim 18, wherein said transition metal is nickel.

23. A method as claimed in claim 18, wherein an enzymatic reaction is carried out in the presence of a chelating agent.

24. The method of claim 23, wherein said chelating agent is selected from the group consisting of ethylenediamine-N,N,N',N'-tetraacetic acid, 1,2-cyclohexanediamine-N,N,N',N'-tetraacetic acid, glycol ether diamine-N,N,N',N'-tetraacetic acid, hexamethylenediamine-N,N,N', N'-tetraacetic acid, hydroxyethyliminodiacetic acid, 1,3-diaminopropan-2-ol-N, N,N',N'-tetraacetic acid, diethylenetriamine-N,N,N',N'',N''-pentaacetic acid, ethylenediamine-N,N'-diacetic acid, ethylenediamine-N,N'-dipropionic acid, N-hydroxyethylethylenediamine-N,N',N'-triacetic acid, and 1,2-diaminopropane-N,N,N',N'-tetraacetic acid, and salts of these acids.

25. The method of claim 23, wherein said chelating agent is present in an amount of from 1 to 100 mM per mM of the transition metal.

26. A method for determining γ-glutamyl transpeptidase activity in a test sample using L-γ-glutamyl-3-carboxy-4-nitroanilide or a salt thereof as a substrate, said method comprising the steps of:

(a) mixing a test sample with component A and component B in any order, wherein said component A comprises L-γ-glutamyl-3-carboxy-4-nitroanilide or a salt thereof as a substrate and a buffer material and wherein component B comprises an amino acid or peptide as a recipient of a γ-glutamyl group and a buffer material, (b) measuring a rate of increase of 3-carboxy-4-nitroaniline released from the substrate, and (c) determining the γ-glutamyl transpeptidase activity in the test sample based on the rate of increase of 3-carboxy-4-nitroaniline, wherein said L-γ-glutamyl-3-carboxy-4-nitroanilide or a salt thereof in step (a) is stabilized by the presence of a transition metal ion or salt.

\* \* \* \* \*